(12) United States Patent
Hirota et al.

(10) Patent No.: US 6,354,144 B1
(45) Date of Patent: Mar. 12, 2002

(54) ZIRCONIA PORCELAIN

(75) Inventors: Toshikazu Hirota, Kuwana; Shigeki Nakao, Nagoya; Kazuyoshi Shibata, Mizunami; Yukihisa Takeuchi, Aichi-prefecture, all of (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 09/272,788

(22) Filed: Mar. 19, 1999

(30) Foreign Application Priority Data

Mar. 27, 1998 (JP) ............................... 10-082328
Mar. 3, 1999 (JP) ............................... 11-055941

(51) Int. Cl.$^7$ ..................... C04B 35/48; H01L 41/08
(52) U.S. Cl. ................. 73/61.49; 73/61.75; 310/321; 310/324
(58) Field of Search ............... 73/61.49, 61.75; 310/316, 321, 324

(56) References Cited

U.S. PATENT DOCUMENTS

| 4,334,974 A | 6/1982 | Muller et al. |
| 4,354,912 A | 10/1982 | Friese |
| 5,877,411 A | * 3/1999 | Namerikawa et al. . 73/61.49 X |
| 5,889,351 A | * 3/1999 | Okumura et al. ............ 310/321 |
| 5,997,671 A | * 12/1999 | Takeuchi et al. .......... 156/89.11 |
| 6,004,644 A | * 12/1999 | Takeuchi et al. ........ 310/324 X |

FOREIGN PATENT DOCUMENTS

| DE | 43 07 727 A1 | 9/1994 |
| EP | 0 671 772 A1 | 9/1995 |
| EP | 0 675 355 A1 | 10/1995 |
| JP | 57-147049 | 9/1982 |
| JP | 60-259952 | 12/1985 |

* cited by examiner

Primary Examiner—Daniel S. Larkin
(74) Attorney, Agent, or Firm—Burr & Brown

(57) ABSTRACT

A $ZrO_2$ porcelain comprising a cylindrical member and a flexible member made of a $ZrO_2$ porcelain which has a relative density not lower than 95% and contains a cubic crystal at a ratio not lower than 75%, thereby exhibiting high erosion resistance and high strength. It is preferable that the $ZrO_2$ porcelain is composed of a tetragonal crystal or a mixture phase consisting of a cubic crystal and a tetragonal crystal or a cubic crystal, a tetragonal crystal and a monoclinic crystal

61 Claims, 7 Drawing Sheets

FIG.5 - Prior Art
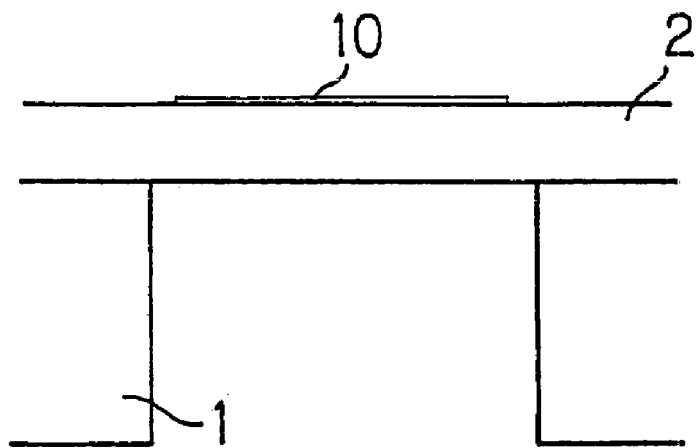
FIG.6 - Prior Art
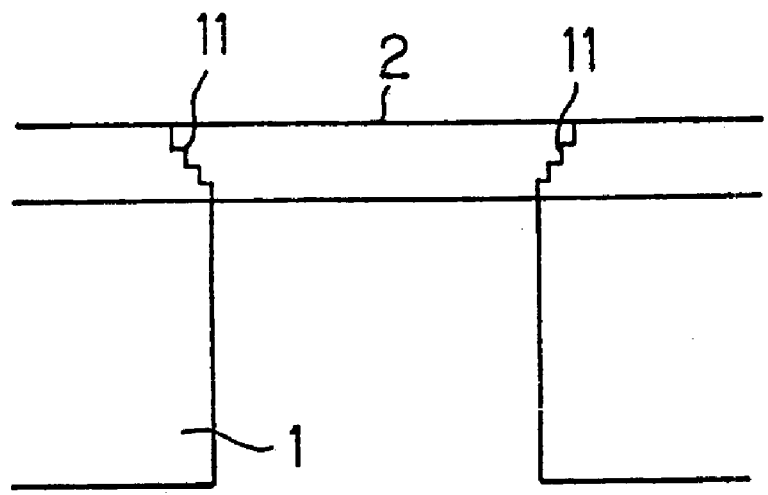

ZIRCONIA PORCELAIN

BACKGROUND OF THE INVENTION AND RELATED ART STATEMENT

The present invention relates to a $ZrO_2$ porcelain and a waterproof $ZrO_2$ member which are to be used as members of a fluid sensor or the like A $ZrO_2$ porcelain is widely used as a material comprising an vibrating sheet which is used for disposing a piezoelectric/electrostrictive element in a fluid sensor. The fluid sensor usually comprises a sensor unit which consists of a plate like member 2 having a piezoelectric/electrostrictive element 10 mounted thereon and a cylindrical member 1 which supports the sensor unit, for example, as shown in FIG. 5. The fluid sensor is configured to allow a sample fluid to be introduced into the cylindrical member 1 and used to measure, for example, a degree of deterioration of a battery by detecting a viscosity, density of the electrolyte or a specific compound in the electrolyte. Both the plate like member 2 and the cylindrical member 1 are made of $ZrO_2$. Ordinarily used as such, a $ZrO_2$ is a partially stabilized $ZrO_2$ which contains 3 to 4 mol % of yttria.

However, the $ZrO_2$ which contains 3 to 4 mol % of yttria poses a problem that it is low in long-term durability and reliability, though it is sufficient in its strength. Speaking concretely, it poses problems described below when it is kept in contact with a liquid or a gas which contains a liquid vapor for a long term, for example, in a condition used as a member of a fluid sensor.

When the fluid sensor is used to evaluate deterioration of a battery, for example, it evaluates a degree of deterioration by utilizing a definite relationship of a viscosity, density of a deteriorated electrolyte of the battery versus a concentration of sulfuric acid and a fact that a concentration of sulfuric acid changes in an electrolyte as the battery is deteriorated. In this case, an acid solution used as the electrolyte is kept in direct contact with the vibrating sheet and the cylindrical member. The vibrating sheet and the cylindrical member may be eroded when they are kept in contact with the acid solution continuously for a very long term, for example, several to some tens of years though no problem is posed in use for a relatively short term. The inventor et al. conducted accelerated tests by keeping vibrating sheet of $ZrO_2$ porcelains in continuous contact with 40% sulfuric acid at 80° C. and found a problem that a porcelain containing yttria at 3 mol allowed the sulfuric acid to leak to an opposite surface of the surface where sulfuric acid contact in Five to thirty days and a porcelain containing yttria at 4 mol allowed the sulfuric acid to leak to a side opposite to an vibrating sheet in ten to Forty days.

It is considered that the leakage is traced to gradual transformation of a tetragonal phase, out of the $ZrO_2$ crystalline structures, into a monoclinic phase which is caused when $ZrO_2$ is left standing in a liquid or a gas containing a liquid vapor.

Though it can be considered to change the crystalline structure of $ZrO_2$ into a cubic crystal which is stable in a liquid or a gas containing a liquid vapor in order to avoid such inconvenience, the cubic crystal has low toughness and is fragile, thereby posing a problem that cracks 11 are formed as shown in FIG. 6 at portions of an integral structure consisting of an vibrating sheet and a cylindrical member on which stresses are concentrated.

Furthermore, there is available a method which makes a $ZrO_2$ porcelain stable in a liquid or a gas containing a liquid vapor by reducing a particle size of a raw material powder or using an additive, such as magnesia or alumina. However, this method poses a problem that it makes stability of the $ZrO_2$ porcelain insufficient and requires high temperature to sinter a piezoelectric/electrostrictive element which is disposed on a vibrating sheet, thereby enlarging the particle size and lowering the stability.

SUMMARY OF THE INVENTION

The present invention has been achieved in view of the circumstances described above and has an object to provide a $ZrO_2$ porcelain which is not only stable but also tough, can hardly be eroded and has sufficient strength in a liquid or a gas containing liquid vapor.

That is, the present invention provides a $ZrO_2$ porcelain comprising a $ZrO_2$ porcelain flexible member having at least a part which is brought into contact with a liquid or a gas containing a liquid vapor,.wherein the contact part has a relative density (bulk density/theoretical density) not lower than 95% and contains a cubic crystal at a ratio not lower than 75%.

In the $ZrO_2$ porcelain, it is preferable that the $ZrO_2$ flexible member consists of a contact part and a substrate adjacent to the contact part, and that the substrate is composed of a tetragonal crystal or a mixture phase consisting of a cubic crystal and a tetragonal crystal or a cubic crystal, a tetragonal crystal, and a monoclinic crystal. Furthermore, it is preferable that the contact part covers at least one surface of the substrate and that a thickness of the contact part is 0.2 to 2 times of that of a thinnest portion of the substrate.

The $ZrO_2$ porcelain may consist of a cylindrical member made of a $ZrO_2$ porcelain and a $ZrO_2$ porcelain flexible member which is composed by disposing a contact part at least on one surface of a plate like member consisting of the substrate, and having an integral structure obtained by integrating the $ZrO_2$ porcelain flexible member with the cylindrical member which is a supporting member for the flexible member so that an end surface of the cylindrical member is brought into contact with the contact part disposed on the plate like member and the contact part closes an opening of the cylindrical member.

Furthermore, the $ZrO_2$ porcelain may consist of a cylindrical member made of a $ZrO_2$ porcelain and a $ZrO_2$ porcelain flexible member which is composed by disposing a contact part at least on one surface of a plate like member consisting of the substrate, comprise a connecting layer which is formed on at least one end surface of the cylindrical member and has a configuration which is the same as that of the contact part, and having an integral structure which is obtained by integrating the $ZrO_2$ porcelain flexible member with the cylindrical member which is a supporting member for the flexible member so that the connecting layer is brought into contact with the contact part disposed on the plate like member and the contact part closes an opening of the cylindrical member.

Furthermore, the $ZrO_2$ porcelain may consist of a cylindrical member made of a $ZrO_2$ porcelain and a $ZrO_2$ porcelain flexible member which is a plate like member consisting of the contact part, and have an integral structure obtained by integrating the $ZrO_2$ porcelain flexible member with the cylindrical member which is a supporting member for the flexible member so that an end surface of the cylindrical member is brought into contact with the plate like member and the contact part closes an opening of the cylindrical member.

Furthermore, the $ZrO_2$ porcelain may consist of a cylindrical member made of a $ZrO_2$ porcelain and a $ZrO_2$ porcelain flexible member which is a plate like member consisting of the contact part, comprise a connecting layer which is formed on at least one end surface of the cylindrical member and has the same configuration as that of the contact part, and have an integral structure obtained by integrating the $ZrO_2$ porcelain flexible member with the cylindrical member which is a supporting member for the flexible member so that the connecting layer is brought into contact with the plate like member and the contact part closes an opening of the cylindrical member.

For the $ZrO_2$ porcelain according to the present invention, it is preferable to dispose a contact part which has a relative density (bulk density/theoretical density) not lower than 95% and contains a cubic crystal at a ratio not lower than 75%, on inside walls of a space formed by the $ZrO_2$ porcelain flexible member and the cylindrical member which is a supporting member for the flexible member.

The $ZrO_2$ porcelain according to the present invention may comprise a cylindrical member made of a $ZrO_2$ porcelain; and a plate like member composed of the substrate, wherein an end surface of the cylindrical member is in contact with the plate like member, a contact part which has a relative density (bulk density/theoretical density) not lower than 95% and contains a cubic crystal at a ratio not lower than 75% is disposed on inside walls of a space formed by closing an opening of said cylindrical member, and a $ZrO_2$ porcelain flexible member is integrated with the cylindrical member which is a supporting member for the flexible member.

In the $ZrO_2$ porcelain according to the present invention, the cylindrical member may be composed of a substrate which consists of a tetragonal crystal or a mixture phase consisting of a cubic crystal and a tetragonal crystal or a cubic crystal, a tetragonal crystal, and a monoclinic crystal, the cylindrical member may be composed of a contact part which has a relative density (bulk density/theoretical density) not lower than 95% and contains a cubic crystal at a ratio not lower than 75% or the cylindrical member may be composed of an intermediate layer which contains a cubic crystal at a ratio higher than the substrate and lower than the contact part. Furthermore, the $ZrO_2$ porcelain according to the present invention may have an integral structure of a cover member and a cylindrical member wherein the cover member is attached to the other end surface of the cylindrical member so as to close an opening of the cylindrical member and a hole formed in the cover member communicates with an internal space of the cylindrical member. In this case, the cover member may be composed of a substrate which consists of a tetragonal crystal or a mixture phase consisting of a cubic crystal and a tetragonal crystal or a cubic crystal, a tetragonal crystal and a monoclinic crystal. In the $ZrO_2$ porcelain according to the present invention, an intermediate $ZrO_2$ layer which contains a cubic crystal at a ratio higher than the substrate or the cylindrical member and lower than the contact part or the connecting layer may be disposed at least at a location between the substrate or the cylindrical member and the contact part or the connecting layer, and it is preferable that the intermediate $ZrO_2$ layer contains a cubic crystal at a ratio not lower than 60% and not higher than 95%. The $ZrO_2$ porcelain according to the present invention may comprise a piezoelectric/electrostrictive element which is disposed on a surface of the $ZrO_2$ porcelain flexible member. Furthermore, the $ZrO_2$ porcelain according to the present invention may contain lead.

Moreover, the present invention provides a fluid sensor which uses the $ZrO_2$ porcelain described above. Furthermore, the present invention provides a fluid sensor comprising: a piezoelectric element having a piezoelectric film and at least a pair of electrodes disposed in contact with said piezoelectric film, on the opposite surface of the surface where said cylindrical member is located, of said $ZrO_2$ porcelain flexible member composing the $ZrO_2$ porcelain described above, electrode terminals disposed on the opposite surface of the surface where said cylindrical member is located, of said $ZrO_2$ porcelain flexible member and electrically connected to said pair of electrodes; a supporting member fixing said $ZrO_2$ porcelain flexible member; and a separating member maintaining said piezoelectric element and said supporting member in contactless conditions; wherein said separating member is disposed on the opposite surface of the surface where said cylindrical member is located, of said $ZrO_2$ porcelain flexible member so as to surround said piezoelectric element, and said supporting member is in contact with said $ZrO_2$ porcelain flexible member and fix it by way of said separating member, characterized in that a glass layer is formed on the opposite surface of the surface where said cylindrical member is located, of said $ZrO_2$ porcelain flexible member which is kept in contact with said separating member.

In addition, the present invention provides a waterproof $ZrO_2$ member to be used in an atmosphere containing water or water steam, wherein a substrate is made of $ZrO_2$ which is is composed of a tetragonal crystal or a mixture phase consisting of a cubic crystal and a tetragonal crystal or a cubic crystal, a tetragonal crystal, and a monoclinic crystal, and a $ZrO_2$ layer which has a relative density (bulk density/theoretical density) not lower than 95% and contains a cubic crystal at a ratio not lower than 75% is disposed at a location to be exposed to an atmosphere containing water or water steam. The atmosphere containing water or water steam may be an acidic atmosphere.

BRIEF DESCRIPTION OF THE DRAWINGS

FIG. 5 is a schematic sectional view showing a configuration of a fluid sensor.

FIG. 6 is a schematic sectional view exemplifying a conventional $ZrO_2$ porcelain.

FIG. 9(*b*) is a schematic sectional view of FIG. 9(*a*).

DETAILED DESCRIPTION OF PREFERRED EMBODIMENT

Figure 1:
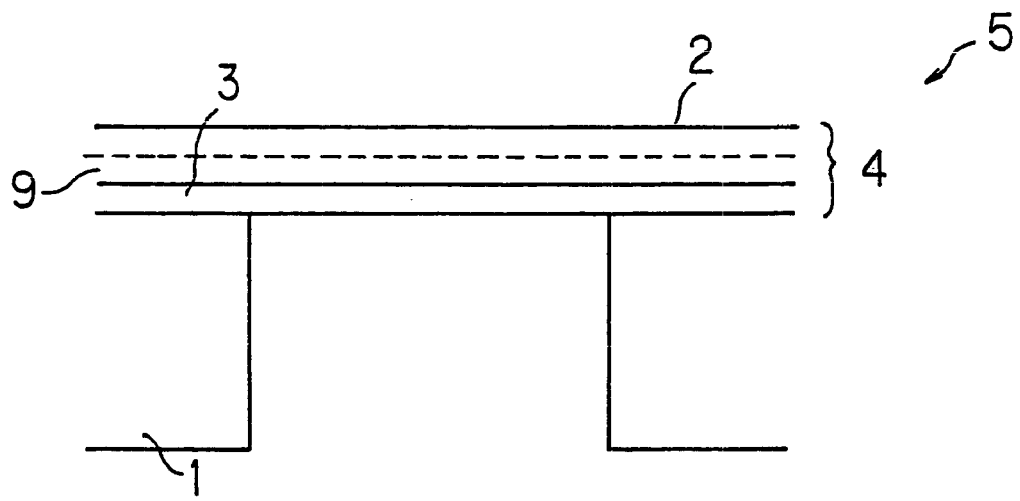
FIGS. 1(*a*) and 1(*b*) are schematic sectional views showing an embodiment and another embodiment of the $ZrO_2$ porcelain according to the present invention.
Figure 1:
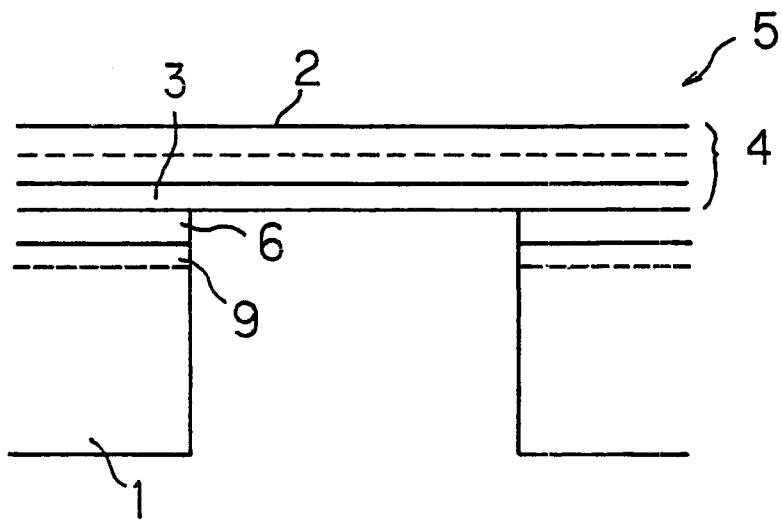

In the $ZrO_2$ porcelain according to the present invention, a part thereof which is to be brought into contact with a liquid or a gas containing a liquid vapor, that is, a contact part has a relative density (bulk density/theoretical density) not lower than 95% and contains a cubic crystal at a ratio not lower than 75%. Since the cubic crystal has a low toughness though it has a crystalline structure which is stable in the liquid or the gas containing the liquid vapor, it is possible to impart to the $ZrO_2$ porcelain a nature that it can hardly be eroded and has high strength by composing only the contact part of a cubic crystal. Speaking concretely, the contact part contains yttria ($Y_2O_3$) at 6 to 15 mol %, preferably 8 to 10 mol % in order to compose the contact part of a cubic crystal.

The relative density (bulk density/theoretical density) is specified at the level not lower than 95% since sufficient strength and airtightness cannot be obtained at a relative density lower than 95%. In addition, it is more preferable that the relative density (bulk density/theoretical density) is 98% or higher. On the other hand, the content of the cubic crystal is defined at the level not lower than 75% since it is impossible to impart sufficient erosion resistance at a cubic crystal content lower than 75%. In addition, it is preferable that the cubic crystal is contained at a ratio not lower than 90% from a viewpoint of the erosion resistance. However, a content of the cubic crystal is to be adequately determined dependently on a desired degree of erosion resistance and a fundamental configuration of a substrate described later since the content of a cubic crystal not lower than 90% makes strength slightly lower than that at a ratio which is not lower than 75% and lower than 90%.

Out of the X-ray diffractometry and Raman spectroscopy which are generally used for identifications of various kinds of crystalline phases contained in crystalline systems and calculations of their ratios, the inventor adopts the X-ray diffractometry to determine ratios of existing crystalline phases on the basis of intensity ratios among typical diffracted rays of various kinds of the crystalline phases. Components of zirconium oxide in ceramic substrates are judged using an X-ray diffractometer for thin films in procedures which are described below.

Since a monoclinic crystal and a cubic crystal have crystal lattice surface spacings which are largely different from each other due to a difference in symmetry or their crystal lattices in the crystalline phase of zirconium oxide, the monoclinic crystal and the cubic crystal can be quantitatively determined from a ratio between intensities of main diffracted X-rays. On the other hand, a tetragonal crystal and a cubic crystal which have lattice surface spacings close to each other cannot be separated and quantitatively determined directly and accurately from the main diffracted X-rays. Accordingly, existence of a tetragonal crystal in a sample is confirmed by comparing diffracted X-ray images of the cubic crystal (C): C(111), C(200), C(220), C(311) and C(222) with diffracted X-ray images of the tetragonal crystal (T): T(111), T(002), T(200), T(202), T(220), T(113), T(131) and T(222).

An existing ratio of the cubic crystal is defined as an existing ratio of the cubic crystal relative to the cubic crystal+the tetragonal crystal and a content of the cubic crystal is determined as a ratio between intensities of the main diffracted ray from the crystals. "Contains a cubic crystal at a ratio not lower than 75%" is defined as satisfaction of a condition expressed by [Equation 1].

$$\frac{I \cdot C(111)}{I \cdot T(111) + I \cdot C(111)} \geq 0.75 \qquad \text{[Equation 1]}$$

When it is difficult to separate main diffracted rays from the tetragonal crystal and the cubic crystal which are close to each other, diffracted rays of a higher order may be used in place of the main diffracted rays. In such a case, however, it is necessary to standardize measured intensities of the diffracted rays of the higher order with intensities of the main diffracted rays using values of intensities of the main diffracted rays and those of the diffracted rays of the higher order which are known from the JCPDS card or the like. To determine an existing ratio from intensities of diffracted rays of the cubic crystal (200) and the tetragonal crystal (002)+ (200), for example.

$$\frac{100/25 \times I \cdot C(200)}{100/25 \times I \cdot C(200) + 100/43 \times [I \cdot T(002) + I \cdot T(200)]} \geq 0.75 \qquad \text{[Equation 2]}$$

[Equation 2] is used in place of the condition mentioned above since the JCPDS card indicates 25 and 43 (a sum of (002) and (200)) as intensities of the diffracted rays of the crystals for a (111) intensity 100 of the main diffracted ray.

In addition, symbols used in the numeric formulae are as defined below:

I.T (111): (111) diffraction intensity of tetragonal crystal
I.C (111) (111) diffraction intensity of cubic crystal
I.T (002): (002) diffraction intensity of tetragonal crystal
I.C (200): (200) diffraction intensity of cubic crystal
I.T (200): (200) diffraction intensity of tetragonal crystal The expression "a gas containing a liquid vapor" used herein means a gas which contains a space in the vicinity of a liquid surface or a mist like liquid such as a gas contained in a space in a battery. Furthermore, the $ZrO_2$ porcelain flexible member is a member which is made of a $ZrO_2$ porcelain and partially or entirely bent in use such as vibrating sheet or a diaphragm of a fluid sensor, actuator, or the like.

In the present invention, it is preferable that the $ZrO_2$ porcelain is composed of a contact part and a substrate adjacent to the contact part, and that the substrate is composed of a tetragonal crystal or a mixture phase consisting of a cubic crystal and a tetragonal crystal or a cubic crystal, a tetragonal crystal, and a monoclinic crystal. This composition is preferable to impart a sufficient toughness to the $ZrO_2$ porcelain. Speaking concretely, yttria, for example, is contained in the substrate at 1.5 to 6 mol %, preferably 2.5 to 4.5 mol %, to compose the substrate of a tetragonal crystal, or a mixture phase consisting of a cubic crystal and a tetragonal crystal or a cubic crystal, a tetragonal crystal, and a monoclinic crystal.

Furthermore, it is preferable that the contact part covers at least one surface of the substrate and has a thickness which is 0.2 to 2 times of that of a thinnest portion of the substrate. This thickness is preferable to impart sufficient erosion resistance to the $ZrO_2$ porcelain.

The $ZrO_2$ porcelain according to the present invention may consist of a cylindrical member 1 made of the $ZrO_2$ porcelain and a $ZrO_2$ porcelain flexible member 4 which is composed by disposing a contact part 3 on at least one surface of a plate like member 2 consisting of the substrate as shown in FIG. 1(*a*), and have an integral structure obtained by integrating the $ZrO_2$ porcelain flexible member 4 with the cylindrical member 1 which is a supporting member for the flexible member so that an end surface of the cylindrical member 1 is brought into contact with the contact part 3 disposed on the plate like member 2 and the contact part 3 closes an opening of the cylindrical member 1.

Figure 2:
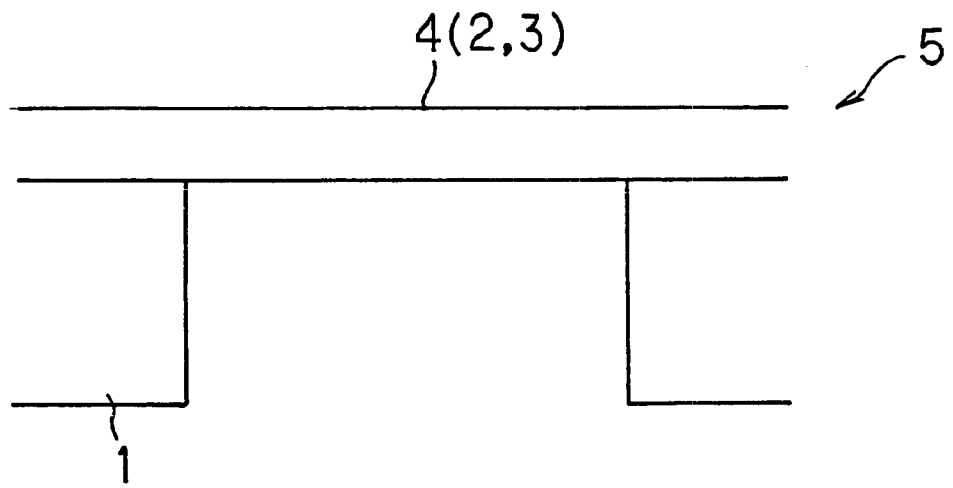
FIGS. 2(*a*) and 2(*b*) are schematic sectional views showing still another embodiment of the $ZrO_2$ porcelain according to the present invention.
Figure 2:
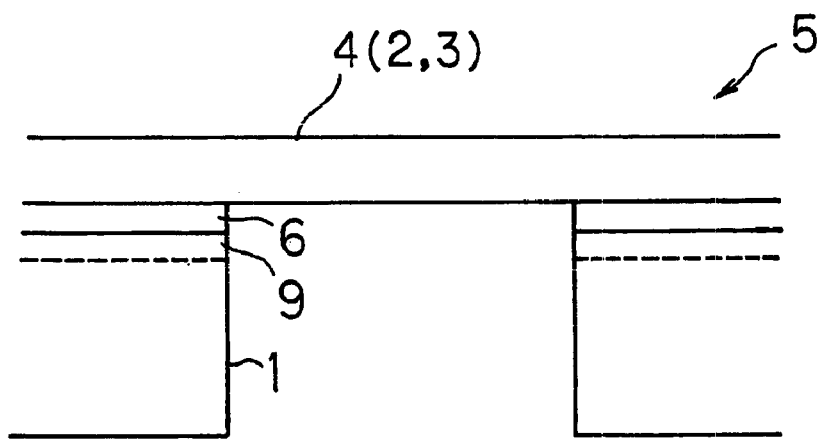

Furthermore, the $ZrO_2$ porcelain according to the present invention may consist of the cylindrical member 1 made of a $ZrO_2$ porcelain and a $ZrO_2$ porcelain flexible member 4 which is a plate like member 2 composed of the contact part 3 as shown in FIG. 2(a), and have an integral structure obtained by integrating the $ZrO_2$ porcelain flexible member 4 with the cylindrical member 1 which is the supporting member for the flexible member so that an end surface of the cylindrical member 1 is brought into contact with the plate like member 2 and the contact part 3 closes an opening of the cylindrical member 1. Though the $ZrO_2$ porcelain flexible member 4 itself has a low toughness and is fragile when the $ZrO_2$ porcelain flexible member 4 is composed of the contact part which contains a cubic crystal at a high ratio, a $ZrO_2$ porcelain 5 as a whole can maintain sufficient strength since it is supported by the cylindrical member 1.

Furthermore, the $ZrO_2$ porcelain according to the present invention may comprise a connecting layer 6 which has the same composition as the contact part and is disposed between at least one end surface of the cylindrical member 1 and the contact part 3 of the $ZrO_2$porcelain flexible member 4 as shown in FIGS. 1(b) and 2(b). When the $ZrO_2$ porcelain is used, for example, as a fluid sensor to evaluate deterioration of a battery and cracks are formed in the contact part 3 which has low toughness due to stresses produced by transformation of the cylindrical member 1, the connecting layer 6 is capable of preventing cracks from being formed, and sulfuric acid from leaking to an opposite surface of the surface of vibrating sheet where sulfuric acid contact.

Figure 3:
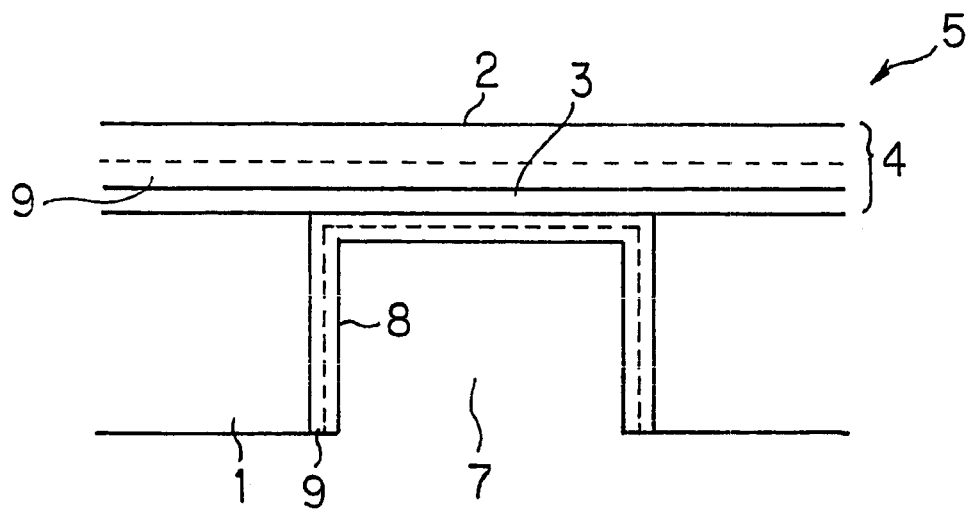
FIG. 3 is a schematic sectional view showing still another embodiment of the $ZrO_2$ porcelain according to the present invention.

In the $ZrO_2$ porcelain according to the present invention which has an integral structure as described above, a layer 8 which has a relative density (bulk density/theoretical density) not lower than 95% and contains a cubic crystal at a ratio not lower than 75% may further be disposed on the inside walls of a space 7 formed by he $ZrO_2$ porcelain flexible member 4 and the cylindrical member 1 which is the supporting member for the flexible member as shown in FIG. 3. This configuration makes it possible to impart sufficient erosion resistance to all contact parts, and strengthen a seam between the $ZrO_2$ porcelain flexible member 4 and the cylindrical member 1 which is liable to be cracked due to stresses.

Figure 4:
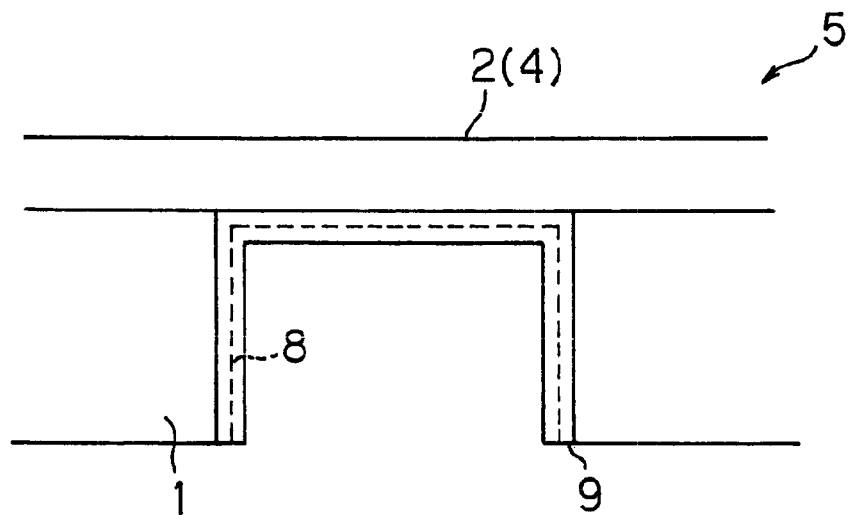
FIG. 4 is a schematic sectional view showing still another embodiment of the $ZrO_2$ porcelain according to the present invention.

In the $ZrO_2$ porcelain according to the present invention, a layer which has a relative density (bulk density/theoretical density) not lower than 95% and contains a cubic crystal at a ratio not lower than 75% may be disposed only on inside walls of a space 7 formed by closing the opening of the cylindrical member 1 as shown in FIG. 4. When such a layer is formed on the entire surfaces of the inside walls, the contact parts preferably have sufficient erosion resistance.

Strength of the $ZrO_2$ porcelain according to the present invention can be further enhanced as a whole by composing the cylindrical member of a tetragonal crystal or a mixture phase of a cubic crystal and a tetragonal crystal or a cubic crystal, a tetragonal crystal, and a monoclinic crystal. The seam between the $ZrO_2$ porcelain flexible member and the supporting member which is liable to be cracked due to stresses can be further strengthened by forming an intermediate $ZrO_2$ layer 9 which contains a cubic crystal at a ratio higher than the substrate or the cylindrical member and lower than the contact part or the connecting layer at least at a location between the substrate or the cylindrical member and the contact part or the connecting layer as shown in FIGS. 1 through 4. It is preferable that the intermediate $ZrO_2$ layer 9 contains the cubic crystal at a ratio not lower than 60% and not higher than 95% on a premise that the intermediate $ZrO_2$ layer contains the cubic crystal at a ratio higher than the substrate or the cylindrical member and lower than the contact part or the connecting layer. Speaking concretely, such an intermediate $ZrO_2$ layer 9 can be obtained, for example, by allowing the intermediate $ZrO_2$ layer 9 to contain yttria at 5 to 7 mole %, preferably 5.5 to 6.5 mol %.

In the $ZrO_2$ porcelain according to the present invention, a cubic crystal content of the cylindrical member may be higher than that of the substrate and lower than that of the contact part described above. Such a cubic crystal content of the cylindrical member provides a merit to make erosion resistance compatible with strength. Mentioned as such a $ZrO_2$ porcelain is, for example, a $ZrO_2$ porcelain consisting of a $ZrO_2$ porcelain flexible member 4 which comprises a substrate, a contact part 3 and an intermediate layer 9, and a cylindrical member 1 as shown in FIG. 1(a), wherein the cylindrical member 1 contains a cubic crystal at a ratio not lower than 60% and not higher than 95%. Speaking of concrete means to obtain a cubic crystal content within the range specified above, yttria, for example, is contained in the cylindrical member 1 at 5 to 7 mol %, preferably 5.5 to 6.5 mol %.

In the $ZrO_2$ porcelain according to the present invention, the cylindrical member may have a relative density (bulk density/theoretical density) of 95% or higher and contain a cubic crystal at 75% or higher. Such a cylindrical member can enhance erosion resistance of the $ZrO_2$ porcelain. In this case, the cylindrical member contains yttria at 6 to 15 mol %, preferably 8 to 10 mol %. In this case, however, toughness of the cylindrical member is lowered, whereby strength of the $ZrO_2$ porcelain may be insufficient. Accordingly, it is preferable to use the cylindrical member in combination with a cover member which is described later.

Figure 7:
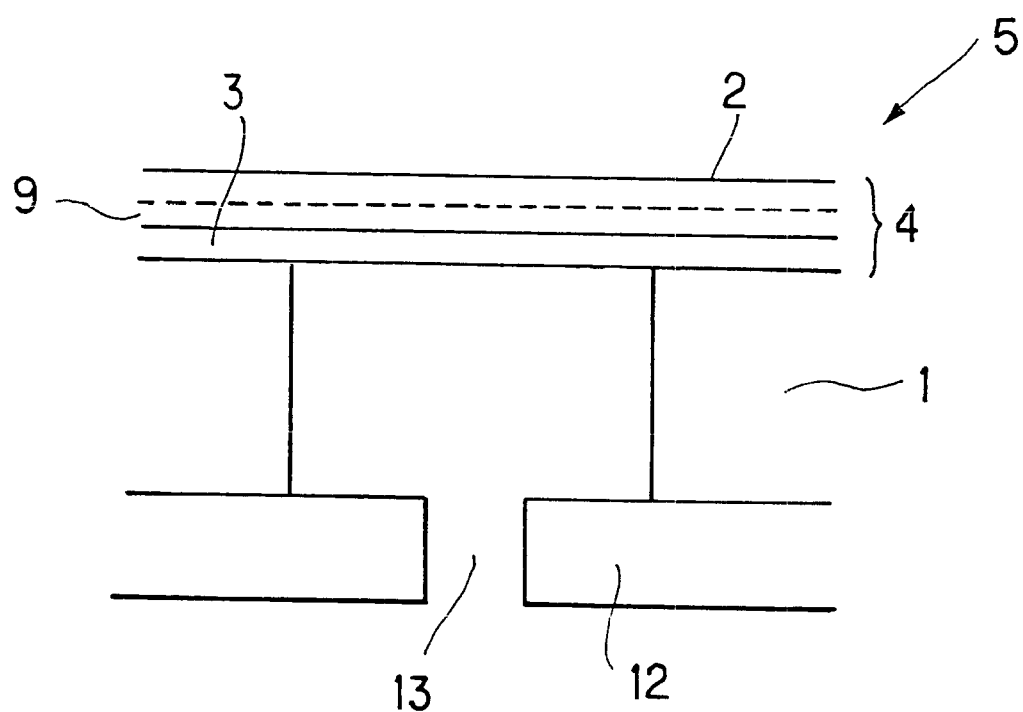
FIG. 7 is a schematic sectional view showing further another embodiment of the $ZrO_2$ porcelain according to the present invention.

Strength of the $ZrO_2$ porcelain according to the present invention as a whole can be enhanced by attaching a cover member 12 to an end surface of the cylindrical member 1 different from the end surface on which the $ZrO_2$ flexible member 4 is disposed so that the cover member 12 covers the opening of the cylindrical member 1 and integrating the cover member 12 with the cylindrical member 1 so that a hole 13 formed in the cover member 12 communicates with the internal space of the cylindrical member 1 as shown in FIG. 7. When the $ZrO_2$ porcelain is to be used as a fluid sensor, the cover member 12 hardly allows external noise to enter the vibrating member. In this case, it is preferable to compose the cover member 12 of a tetragonal crystal or a mixture phase of a cubic crystal and a tetragonal crystal or a cubic crystal, a tetragonal crystal and a monoclinic crystal for enhancing strength of the sensor furthermore.

A $ZrO_2$ porcelain such as a vibrating sheet often contains lead for use of piezoelectric material for adjusting atmosphere and diffusion of substances composing a piezoelectric material when sintering the piezoelectric material. In such a case, the $ZrO_2$ is more liable to be transformed and it is effective to dispose the contact part described above. For the $ZrO_2$ porcelain according to the present invention, erosion resistance may be further enhanced by covering the contact part with an acid-resisting resin, such as polyester resin or an epoxy acrylate resin, glass, or the like. Dipping, spraying, coating, and the like can be mentioned as covering methods.

The ZrO$_2$ porcelain according to the present invention may comprise a piezoelectric/electrostrictive element disposed on a surface of the ZrO$_2$ porcelain flexible member so that it can be used as a fluid sensor, an actuator, or the like. In such a case, the piezoelectric/electrostrictive element is disposed on the substrate of the ZrO$_2$ porcelain flexible member.

Figure 8:
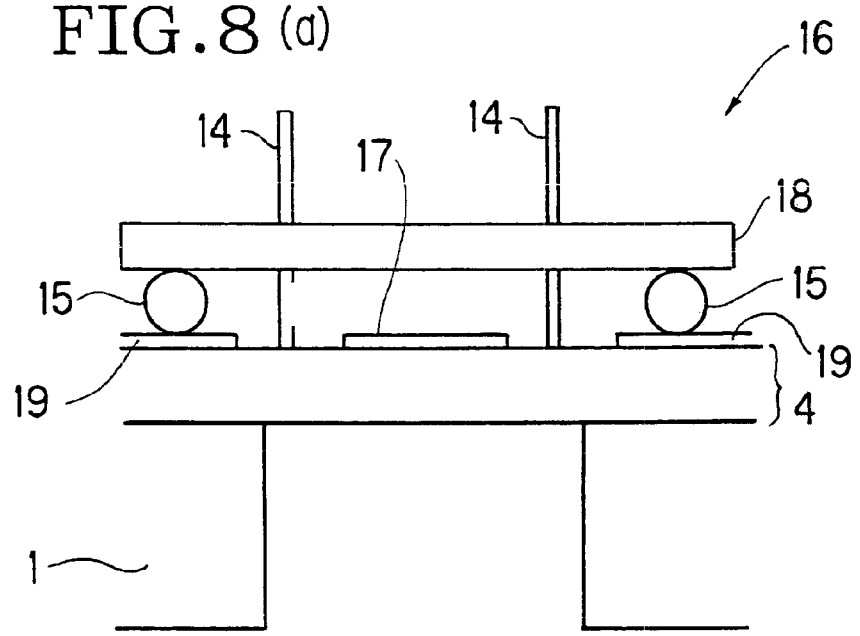
FIGS. 8(*a*) and 8(*b*) are schematic sectional views showing further another embodiment of the $ZrO_2$ porcelain according to the present invention.
Figure 8:
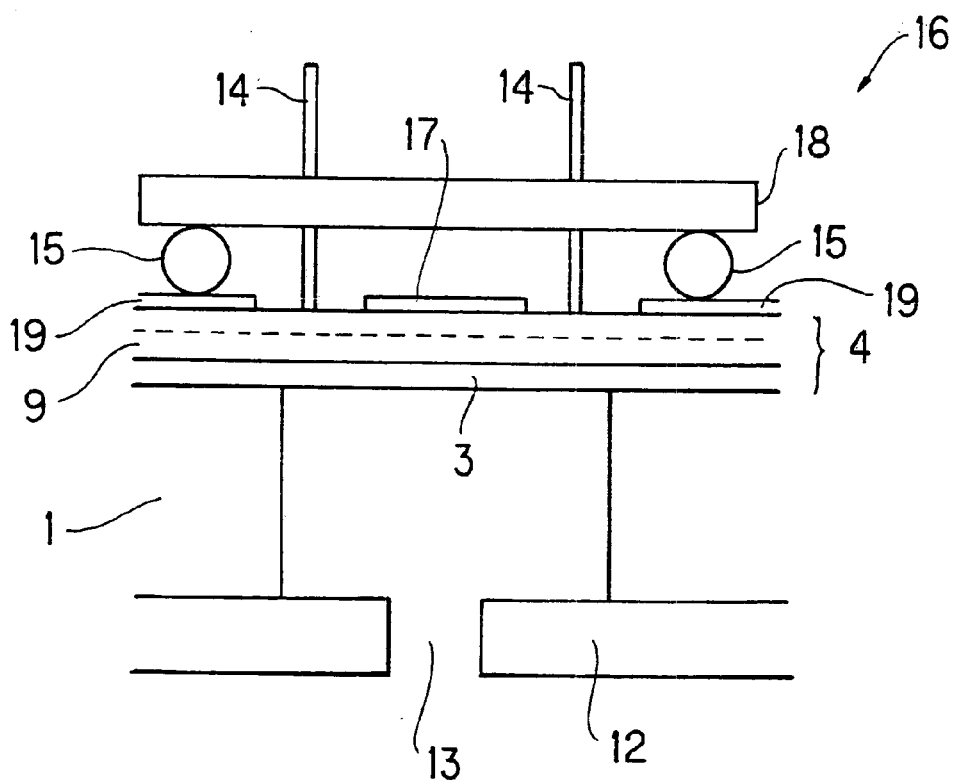

A fluid sensor which uses the ZrO$_2$ porcelain according to the present invention may comprise a separating member 15 and a supporting member 18 as shown in FIG. 8. In a fluid sensor 16 shown in FIG. 8, the separating member 15 and the supporting member 18 are disposed to maintain a piezoelectric/electrostrictive element 17 and electrode terminals disposed on a surface of a ZrO$_2$ porcelain flexible member 4 in a condition airtight from a fluid. Since the piezoelectric/electrostrictive element 17 vibrates the ZrO$_2$ porcelain flexible member 4, the separating member 15 which is adopted to prevent the supporting member 18 from being brought into contact with the piezoelectric/electrostrictive element 17 is disposed so as to surround the piezoelectric/electrostrictive element 17. Connected to the electrode terminals are lead wires 14 which are externally distributed through holes formed in the supporting member 18. The holes are maintained airtight with an adhesive agent or the like. Furthermore, a glass layer 19 is formed on the ZrO$_2$ porcelain flexible member 4 at a location which is in contact with the separating member 15. This glass layer 19 is formed to maintain the separating member 15 in an airtight condition for a long term on the ZrO$_2$ porcelain flexible member 4. That is, in a fluid sensor having such a configuration as described above, the whole sensor is usually used in a condition where the sensor is submerged in a fluid. Since all parts are kept in contact with the fluid in such a case, except for the parts which are kept airtight by the separating member 15 and the supporting member 18, the substrate is kept in contact with the fluid and eroded in long-term use on the surface of the ZrO$_2$ porcelain flexible member 4 which is outside the separating member 15, whereby the maintenance of airtightness by the separating part 15 is degraded after long-term use. The glass layer 19 is provided to prevent such a situation.

Figure 9:
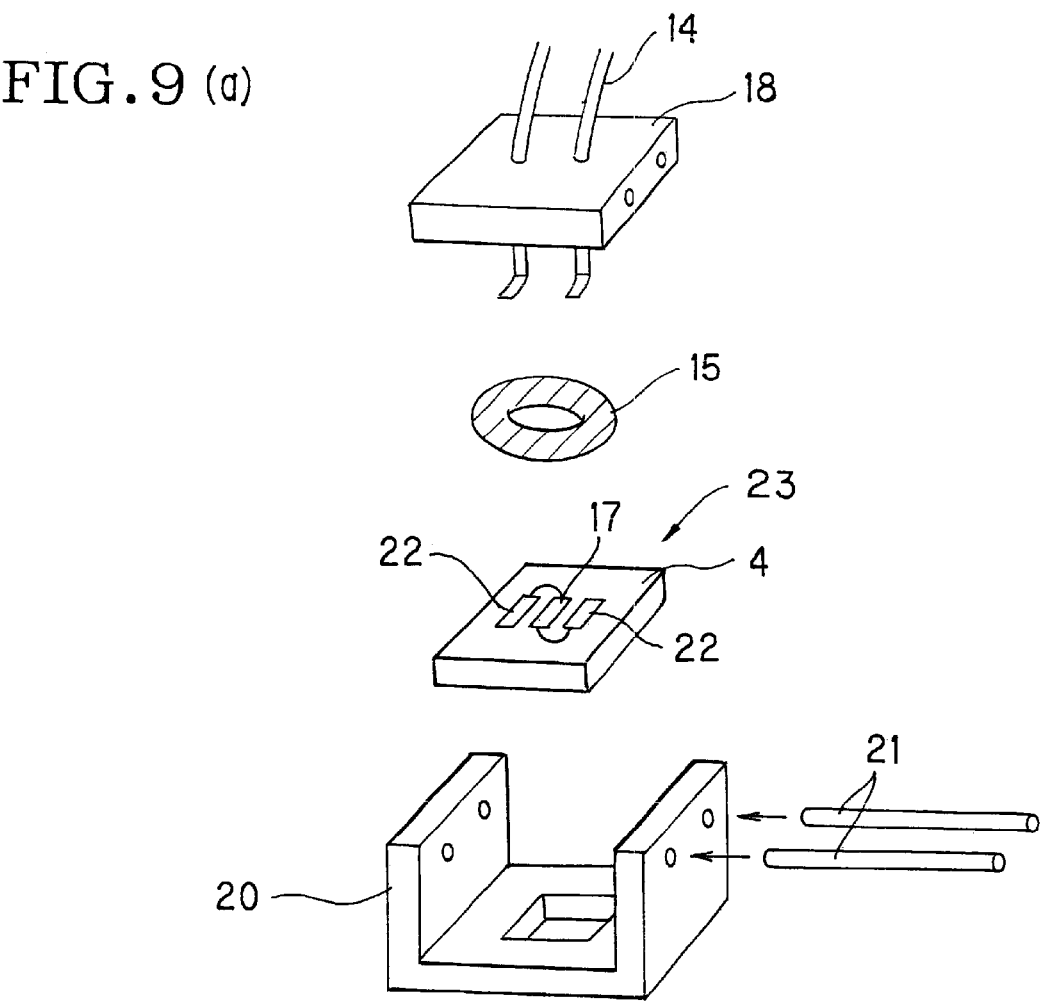
FIG. 9(*a*) is a schematic perspective view showing further another embodiment of the $ZrO_2$ porcelain according to the present invention.
Figure 9:
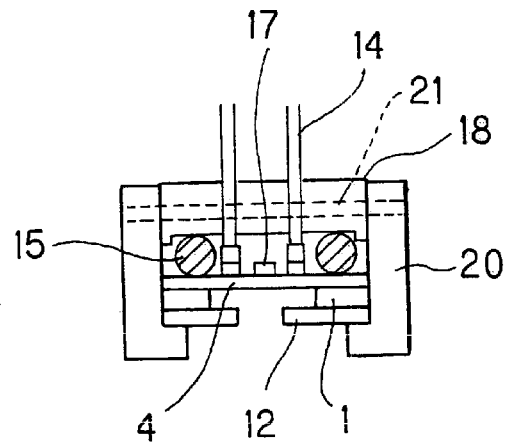

The separating member 15 is not restricted in particular in its shape and may be a block member which has a square section. From a viewpoint to maintain airtightness, it is preferable to use a member which is like an O-ring having a circular section. Furthermore, it is preferable that the separating member 15 is made of a material which has not only erosion resistance against a fluid but also a cushioning property from a viewpoint of airtightness. When the separating member 15 is made of a cushioning material, it is effective to suppress unwanted vibrations of the ZrO$_2$ porcelain flexible member 4 and provides a merit to enhance an accuracy of the sensor. And the supporting member 18 is neither restricted in its shape nor material. The supporting member 18 is sufficiently effective so far as it cooperates with the separating member 15 to sustain the ZrO$_2$ porcelain flexible member 4 and the cylindrical member 1, and maintain the piezoelectric/electrostrictive element 17 and the electrode terminals airtight from a fluid. A fluid sensor which is shown in FIGS. 9(*a*) and 9(*b*), for example, adopts a configuration wherein a sensor element 23 which is composed of a ZrO$_2$ porcelain flexible member 4, a cylindrical member 1, a cover member 12, a piezoelectric/electrostrictive element 17 and electrode terminals 22 are enclosed by a supporting member 18 made of vinyl chloride, a separating member 15 consisting of an O-ring made of a fluoro-rubber, and a clamp member 20 made also of a vinyl chloride, and sustained by an elasticity of the separating member 15. These members are fixed by passing a shaft body 21 through holes formed in the supporting member 18 and the clamp member 20. From viewpoints of strength and erosion resistance, it is preferable that the shaft body 21 is made of a ceramic material or a glass material though it can also be made of vinyl chloride.

In order to enhance erosion resistance of the fluid sensor shown in FIG. 8 or 9, it is preferable that the cylindrical member 1 has a relative density (bulk density/theoretical density) not lower than 95% and contains a cubic crystal at a ratio not lower than 75%. Furthermore, it is preferable that the ZrO$_2$ porcelain flexible member 4 consists of a substrate, a contact part 3, and an intermediate layer 9 which is disposed between the substrate and the contact part 3 as shown in FIG. 8(*b*), and contains a cubic crystal at a ratio higher than the substrate and lower than the contact part. Furthermore, it is preferable that the fluid sensor 16 comprises a cover member 12 which is attached, so as to cover an opening of the cylindrical member 1, to an end surface of the cylindrical member 1 different from the end surface to which the ZrO$_2$ porcelain flexible member 4 is attached and has a hole 13 communicating with an internal space of the cylindrical member 1 as shown in FIG. 8(*b*).

When the ZrO$_2$ porcelain according to the present invention is to be used, a fluid sensor and the ZrO$_2$ porcelain flexible member has a width of 0.3 to 0.5 mm, it is preferable that the ZrO$_2$ porcelain flexible member has a thickness of 10 to 50 µm. In this case, it is preferable that the substrate is 5 to 30 µm thick and the contact part is 5 to 30 µm thick. When the intermediate layer is to be formed, it is preferable to configure it so as to have a thickness of 5 to 15 µm. If these parts have thicknesses exceeding the values specified above, the ZrO$_2$ porcelain flexible member will have a large thickness as a whole, thereby suppressing vibrations. If these parts have thicknesses smaller than the values specified above, ZrO$_2$ porcelain strength will be insufficient for the substrate, erosion resistance will be insufficient for the contact part, and maintenance of stress moderating function and continuity to the substrate and the contact part will be insufficient for the intermediate layer.

EXAMPLES

The present invention will be described in more detail below with reference to its examples which are presented not in limitative sense.

Example 1

We manufactured a ZrO$_2$ porcelain for a fluid sensor consisting of a cylindrical member and a vibrating sheet, wherein a contact part disposed on the vibrating sheet was in contact with a connecting layer disposed on the cylindrical member as shown in FIG. 1(*b*).

First, we prepared a green sheet 10 µm thick which was to be used as a vibrating sheet and a green sheet 330 µm thick which was to be used as a cylindrical member. ZrO$_2$ containing 2 to 4 mol % of yttria was used for preparation of the green sheets.

Then, an intermediate layer which was composed of a ZrO$_2$ containing 6 mol % of yttria was formed by screen printing or green sheet lamination-thermocompression bonding on a side of the green sheet for the vibrating sheet which was to be brought into contact with an acid. The intermediate layer was 6 µm thick.

A contact part which was composed of ZrO$_2$ containing 8 mol % of yttria was formed by screen printing or green sheet lamination-thermocompression bonding on the intermediate layer which was formed on the green sheet for the vibrating sheet The contact part was 9 μm thick.

An intermediate layer which was composed of a $ZrO_2$ containing 6 mol % of yttria was formed by screen printing or green sheet lamination-thermocompression bonding on an end surface of the green sheet for the cylindrical member. The intermediate layer was 25 μm thick.

A connecting layer which was composed of $ZrO_2$ containing 8 mol % of yttria was formed by screen printing or green sheet lamination-thermocompression bonding on the intermediate layer which was formed on the green sheet for the cylindrical member. The connecting layer was 25 μm thick.

A cylindrical green sheet was prepared by forming a through hole in the green sheet for the cylindrical member.

Finally, the green sheet for the vibrating sheet was laminated with the cylindrical green sheet so that the green sheet for the vibrating sheet closed an opening of the cylindrical green sheet and the green sheets were sintered at 1450° C. for two hours, thereby obtaining a $ZrO_2$ porcelain.

Using the $ZrO_2$ porcelain as a fluid sensor, we checked it for the number of days elapsed until 40% sulfuric acid at 80° C. leaked to a surface of the vibrating sheet on a side opposite to the cylindrical member.

Example 2

We manufactured a $ZrO_2$ porcelain for a fluid sensor consisting of a cylindrical member and vibrating sheet, wherein a contact part disposed on the vibrating sheet was in contact with an end surface of the cylindrical member and a layer which had a relative density (bulk density/theoretical density) not lower than 95% and contained a cubic crystal at a ratio not lower than 75% was formed on inside walls of the cylindrical member as shown in FIG. 3.

The $ZrO_2$ porcelain was the same as that in Example 1, except for the intermediate layer and the connecting layer which were formed on the end surface of the green sheet for the cylindrical,member in Example 1. However, a contact part was formed on the inside wall of the cylindrical member in procedures described below:

First, an intermediate layer which was composed of $ZrO_2$ containing 6 mol % of yttria was formed by screen printing (through hole printing) or dipping. Formed on the intermediate layer was a connecting layer which was composed of $ZrO_2$ containing 8 mol % of yttria by the same way described above. The intermediate layer and the connecting layer were 6 μm and 13 μm thick respectively.

Using the $ZrO_2$ porcelain described above as a fluid sensor, we checked it for the number of days elapsed until 40% sulfuric acid at 80° C. leaked to a surface of the vibrating sheet on a side opposite to the cylindrical member.

Example 3

We manufactured a $ZrO_2$ porcelain which was to be used as a fluid sensor consisting of a cylindrical member and a vibrating sheet, wherein the vibrating sheet was joined to an end surface of the cylindrical member so as to close an opening of the cylindrical member and a layer which had a relative density (bulk density/theoretical density) not lower than 95% and contained a cubic crystal at a ratio not lower than 75% was formed on inside walls of a space formed by the cylindrical member and the vibrating sheet as shown in FIG. 4.

First, we prepared a green sheet for a vibrating sheet and a green sheet for a cylindrical member. Thicknesses and yttria contents of the green sheets were the same as those is in Example 1.

A through hole was formed in the green sheet for the cylindrical member, the green sheet for the vibrating sheet was laminated with the cylindrical green sheet so that the green sheet for the vibrating sheet closed an opening of the cylindrical green sheet and the green sheets were sintered at 1450° C. for two hours.

Finally, an intermediate layer and a contact part were formed by screen printing (through hole printing) or dipping on inside walls of a space formed by the cylindrical member and the vibrating sheet, and a $ZrO_2$ porcelain was obtained by sintering the members. Thicknesses of the intermediate layer and the contact part, yttria contents and sintering conditions were the same as those in Example 1.

Using the $ZrO_2$ porcelain described above as a fluid sensor, we checked it for the number of days elapsed until 40% sulfuric acid at 80° C. leaked to a surface of the vibrating sheet on a side opposite to the cylindrical member.

Example 4

We manufactured a $ZrO_2$ porcelain which is to be used as a fluid sensor consisting of a cylindrical member and vibrating sheet, wherein the vibrating sheet was composed of a contact part and the vibrating sheet was joined to an end surface of the cylindrical member so as to close an opening of the cylindrical member in a condition where a connecting layer formed on the cylindrical member was in contact with the vibrating sheet as shown in FIG. 2(b).

First, we prepared a green sheet for a vibrating sheet and a green sheet for a cylindrical member. A thickness and yttria content of the green sheet for the cylindrical member were the same as those in Example 1. The green sheet for the vibrating sheet was 20 μm thick. The green sheet for the vibrating sheet was composed of $ZrO_2$ containing 8 mol % of yttria.

An intermediate layer and a connecting layer were formed on an end surface of the green sheet for the cylindrical member as in Example 1. The intermediate layer and the connecting layer were 25 μm and 25 μm thick respectively.

A through hole was formed in the green sheet for the cylindrical member, thereby preparing a cylindrical green sheet.

Finally, the green sheet for the vibrating sheet was laminated with the cylindrical green sheet so that the green sheet for the vibrating sheet closed an opening of the cylindrical green sheet and the green sheets were sintered at 1450° C. for two hours, thereby obtaining a $ZrO_2$ porcelain.

Using the $ZrO_2$ porcelain described above as a fluid sensor, we checked it for the number of days elapsed until 40% sulfuric acid at 80° C. leaked to a surface of the vibrating sheet on a side opposite to the cylindrical member.

Example 5

We manufactured a $ZrO_2$ porcelain which was to be used as a fluid sensor consisting of a cylindrical member, a vibrating sheet, and a cover member as shown in FIG. 7. In a $ZrO_2$ porcelain 5 shown in FIG. 7, a vibrating sheet 4 had a substrate, a contact part 3, and an intermediate layer 9 which was formed between the substrate and the contact part 3, and contained a cubic crystal at a ratio higher than the substrate and lower than the contact part. Furthermore, a cover member 12 was attached to an end surface of the cylindrical member 1 different from an end surface to which the vibrating sheet 4 was attached so that the cover member 12 closed an opening of the cylindrical member 1 and has a hole 13 communicating with an internal space of the cylindrical member 1. Furthermore, the cylindrical member 1 had a relative density (bulk density/theoretical density) not lower than 95% and contained a cubic crystal at a ratio not lower than 75% like the contact part 3.

As in Example 1, an intermediate layer which contained 6 mol % of yttria and a contact part which contained 8 mol % of yttria were formed on a green sheet for vibrating sheet like that used in Example 1.

A green sheet for a cylindrical member and a green sheet for a cover member were manufactured using a $ZrO_2$ containing 2 to 4 mol % of yttria.

A through hole was formed in the green sheet for the cylindrical member to prepare a cylindrical green sheet and a hole was formed also in the green sheet for the cover member.

The green sheet for the vibrating sheet was laminated with the cylindrical green sheet so that the green sheet for the vibrating sheet closed an opening of the cylindrical green sheet, the green sheet for the cover member was laminated so as to close the other opening of the cylindrical green sheet and these members were sintered at 1450° C. for two hours, thereby obtaining a $ZrO_2$ porcelain.

Using the $ZrO_2$ porcelain as a fluid sensor, we checked it for the number of days elapsed until it allowed 40% sulfuric acid at 80° C. to leak to a surface of the vibrating sheet on a side opposite to the cylindrical member.

Comparative Example 1

We manufactured a $ZrO_2$ porcelain for a fluid sensor using a cylindrical member and a vibrating sheet both of which were made of a $ZrO_2$ containing 3 mol % of yttria, actually used it as a fluid sensor and checked it for the number of days elapsed until it allowed 40% sulfuric acid at 80° C. to leak to a surface of the vibrating sheet on a side opposite to the cylindrical member.

Though the $ZrO_2$ porcelain manufactured in comparative Example 1 allowed 40% sulfuric acid at 80° C. to leak upon lapse of Five to thirty days, the $ZrO_2$ porcelains manufactured in Examples did not allow 40% sulfuric acid at 80° C. to leak upon lapse of one hundred twenty or more days.

The $ZrO_2$ porcelain according to the present invention can hardly be eroded and has high strength owing to its crystalline structure wherein a portion to be brought into contact with a liquid or a gas containing the liquid vapor is made of a cubic crystal. Accordingly, the $ZrO_2$ porcelain does not allow a liquid such as sulfuric acid to leak to a surface of the vibrating sheet on a side opposite to surface where sulfuric acid contact even when it is used as a fluid sensor or the like, thereby being capable of prolonging service lives of implements which use $ZrO_2$ porcelain flexible members. The $ZrO_2$ porcelain according to the present invention can have more sufficient toughness when a substrate is composed of a tetragonal crystal or a mixture phase consisting of a cubic crystal and a tetragonal crystal or a cubic crystal, a tetragonal crystal, and a monoclinic crystal.

What is claimed is:

1. A $ZrO_2$ flexible diaphragm structure, comprising a supporting member having an opening therein; and
   a $ZrO_2$ porcelain flexible member laminated on an upper surface of said supporting member covering said opening therein, wherein a lower surface of said flexible member exposed to said opening is a contact part to be brought into contact with a liquid or a gas containing a liquid vapor,
   and said contact part has a relative density (bulk density/ theoretical density) not lower than 95% and contains at least 75% cubic crystal phase.

2. The $ZrO_2$ flexible diaphragm structure according to claim 1, wherein said flexible member comprises said contact part and a substrate adjacent to the contact part, and said substrate is composed of a tetragonal crystal, a mixture phase consisting of a cubic crystal and a tetragonal crystal, or a mixture phase consisting of a cubic crystal, a tetragonal crystal and a monoclinic crystal.

3. The $ZrO_2$ flexible diaphragm structure according to claim 2, wherein said contact part covers at least one surface of said substrate and a thickness of said contact part is 0.2 to 2 times of a thickness of a thinnest portion of said substrate.

4. The $ZrO_2$ flexible diaphragm structure according to claim 3,
   wherein said $ZrO_2$ porcelain flexible member is formed by disposing said contact part on at least one surface of a plate like member consisting of said substrate.

5. The $ZrO_2$ flexible diaphragm structure according to claim 4, said supporting member further comprising:
   a connecting layer having a composition which is similar to that of said contact part, said connecting layer being formed at least on one end surface of said supporting member, said connecting layer being in contact with said contact part.

6. The $ZrO_2$ flexible diaphragm structure according to claim 4, wherein a contact layer is provided which has a relative density (bulk density/theoretical density) not lower than 95% and contains at least 75% cubic crystal phase, on the inside walls of a space formed by said flexible member and said supporting member.

7. The $ZrO_2$ flexible diaphragm structure according to claim 4, wherein said supporting member is composed of a tetragonal crystal, a mixture phase consisting of a cubic crystal and a tetragonal crystal, or a mixture phase consisting of a cubic crystal, a tetragonal crystal, and a monoclinic crystal.

8. The $ZrO_2$ flexible diaphragm structure according to claim 4, wherein said supporting member has a relative density (bulk density/theoretical density) not lower than 95% and contains at least 75% cubic crystal phase.

9. The $ZrO_2$ flexible diaphragm structure according to claim 4, wherein said supporting member comprises an intermediate layer which has a cubic crystal content higher than that of said substrate and lower than that of said contact part.

10. The $ZrO_2$ flexible diaphragm structure according to claim 4, wherein a cover member is disposed on the other end surface of said supporting member so as to at least partially cover a second opening of said supporting member and said cover member is integrated with said supporting member so that a hole formed in said cover member communicates with an internal space of said supporting member.

11. A $ZrO_2$ flexible diaphragm structure according to claim 10, wherein said cover member is composed of a cover member substrate which consists of a tetragonal crystal, a mixture phase consisting of a cubic crystal and a tetragonal crystal, or a mixture phase consisting of a cubic crystal, a tetragonal crystal and a monoclinic crystal.

12. A $ZrO_2$ flexible diaphragm structure according to claim 5, wherein said flexible member further comprises an intermediate $ZrO_2$ layer which has a cubic crystal content higher than that of said substrate and lower than that of said contact part between said substrate and said contact part, and/or said supporting member comprises a supporting element and an intermediate $ZrO_2$ layer which has a cubic crystal content higher than that of said supporting element and lower than that of said connecting layer between said supporting element and said connecting layer.

13. The $ZrO_2$ flexible diaphragm structure according to claim 12, wherein said intermediate $ZrO_2$ layer contains said cubic crystal at a ratio not lower than 60% and not higher than 95%.

14. The $ZrO_2$ flexible diaphragm structure according to claim 4, wherein a piezoelectric/electrostrictive element is disposed on a surface of said flexible member.

15. The $ZrO_2$ flexible diaphragm structure according to claim 4 which contains lead.

16. A fluid sensor which uses a $ZrO_2$ flexible diaphragm structure as claimed in claim 4.

17. A fluid sensor comprising:
   a $ZrO_2$ flexible diaphragm structure according to claim 4;
   a piezoelectric element having a piezoelectric film and at least a pair of electrodes disposed in contact with said piezoelectric film, on a first surface of said flexible member which is opposite a second surface of said flexible member which is in contact with said supporting member;
   electrode terminals disposed on said second surface of said flexible member, said electrode terminals being electrically connected to said pair of electrodes;
   a supporting element; and
   a separating member maintaining said piezoelectric element and said supporting element in contactless conditions; wherein said separating member is disposed on said second surface of said flexible member so as to surround said piezoelectric element, and said flexible member is kept in contact and fixed with and to said supporting element by way of said separating member,
   wherein a glass layer is formed on said second surface of said flexible member.

18. The $ZrO_2$ flexible diaphragm structure according to claim 1, further comprising at least one piezoelectric element positioned on a surface of said flexible member opposite said contact part.

19. The $ZrO_2$ flexible diaphragm structure according to claim 1, wherein said supporting member comprises $ZrO_2$ porcelain.

20. A $ZrO_2$ flexible diaphragm structure, comprising:
   a supporting member having an opening therein; and
   a $ZrO_2$ porcelain flexible member consisting of a contact part laminated on an upper surface of said supporting member covering said opening therein, wherein said contact part has a relative density (bulk density/theoretical density) not lower than 95% and contains at least 75% cubic crystal phase.

21. The $ZrO_2$ flexible diaphragm structure according to claim 20, wherein said supporting member comprises a supporting element and a connecting layer, said connecting layer having a composition which is similar to that of said contact part, said connecting layer being formed on at least one end surface of said supporting member, and
   wherein said connecting layer is in contact with said plate like member, and said $ZrO_2$ porcelain flexible member is integrated with said supporting member.

22. The $ZrO_2$ flexible diaphragm structure according to claim 20, wherein a contact layer is provided which has a relative density (bulk density/theoretical density) not lower than 95% and contains at least 75% cubic crystal phase, on the inside walls of a space formed by said flexible member and said supporting member.

23. The $ZrO_2$ flexible diaphragm structure according to claim 20, wherein said supporting member is composed of a tetragonal crystal, a mixture phase consisting of a cubic crystal and a tetragonal crystal, or a mixture phase consisting of a cubic crystal, a tetragonal crystal, and a monoclinic crystal.

24. The $ZrO_2$ flexible diaphragm structure according to claim 20, wherein said supporting member has a relative density (bulk density/theoretical density) not lower than 95% and contains at least 75% cubic crystal phase.

25. The $ZrO_2$ flexible diaphragm structure according to claim 20, wherein said supporting member comprises an intermediate layer which has a cubic crystal content higher than that of said substrate and lower than that of said contact part.

26. The $ZrO_2$ flexible diaphragm structure according to claim 20, wherein a cover member is disposed on the other end surface of said supporting member so as to at least partially cover a second opening of said supporting member and said cover member is integrated with said supporting member so that a hole formed in said cover member communicates with an internal space of said supporting member.

27. A $ZrO_2$ flexible diaphragm structure according to claim 26, wherein said cover member is composed of a cover member substrate which consists of a tetragonal crystal, a mixture phase consisting of a cubic crystal and a tetragonal crystal, or a mixture phase consisting of a cubic crystal, a tetragonal crystal and a monoclinic crystal.

28. A $ZrO_2$ flexible diaphragm structure according to claim 21, wherein said supporting member further comprises an intermediate $ZrO_2$ layer which has a cubic crystal content higher than that of said supporting element and lower than that of said connecting layer between said supporting element and said connecting layer.

29. The $ZrO_2$ flexible diaphragm structure according to claim 28, wherein said intermediate $ZrO_2$ layer contains said cubic crystal at a ratio not lower Than 60% and not higher than 95%.

30. The $ZrO_2$ flexible diaphragm structure according to claim 20, wherein a piezoelectric/electrostrictive element is disposed on a surface of said flexible member.

31. The $ZrO_2$ flexible diaphragm structure according to claim 20 which contains lead.

32. A fluid sensor which uses a $ZrO_2$ flexible diaphragm structure as claimed in claim 20.

33. A fluid sensor comprising:
   a $ZrO_2$ flexible diaphragm structure according to claim 20;
   a piezoelectric element having a piezoelectric film and at least a pair of electrodes disposed in contact with said piezoelectric film, on a first surface of said flexible member which is opposite a second surface of said flexible member which is in contact with said supporting member;
   electrode terminals disposed on said second surface of said flexible member, said electrode terminals being electrically connected to said pair of electrodes;
   a supporting element; and
   a separating member maintaining said piezoelectric element and said supporting element in contactless conditions; wherein said separating member is disposed on said second surface of said flexible member so as to surround said piezoelectric element, and said flexible member is kept in contact and fixed with and to said supporting element by way of said separating member,
   wherein a glass layer is formed on said second surface of said flexible member.

34. The $ZrO_2$ flexible diaphragm structure according to claim 20, further comprising at least one piezoelectric element positioned on a surface of said flexible member opposite said contact part.

35. The $ZrO_2$ flexible diaphragm structure according to claim 20, wherein said supporting member comprises $ZrO_2$ porcelain.

36. A ZrO$_2$ flexible diaphragm structure comprising:
a supporting member having an opening therein;
a flexible member comprising a plate like substrate, an end surface of said supporting member being in contact with said flexible member, said plate like substrate covering said opening; and
a contact layer which has a relative density (bulk density/theoretical density) not lower than 95% and contains at least 75% cubic crystal phase, said contact layer being positioned on inner peripheral walls of said opening in said supporting member and a surface of said plate like substrate surrounded by a region of said contact between said flexible member and said end surface of said supporting member, and said flexible member is integrated with said supporting member.

37. The ZrO$_2$ flexible diaphragm structure according to claim 36, wherein said supporting member is composed of a tetragonal crystal, a mixture phase consisting of a cubic crystal and a tetragonal crystal, or a mixture phase consisting of a cubic crystal, a tetragonal crystal, and a monoclinic crystal.

38. The ZrO$_2$ flexible diaphragm structure according to claim 36, wherein said supporting member has a relative density (bulk density/theoretical density) not lower than 95% and contains at least 75% cubic crystal phase.

39. The ZrO$_2$ flexible diaphragm structure according to claim 36, wherein said supporting member comprises an intermediate layer which has a cubic crystal content higher than that of said substrate and lower than that of said contact layer.

40. The ZrO$_2$ flexible diaphragm structure according to claim 36, wherein a cover member is disposed on the other end surface of said supporting member so as to at least partially cover a second opening of said supporting member and said cover member is integrated with said supporting member so that a hole formed in said cover member communicates with an internal space of said supporting member.

41. A ZrO$_2$ flexible diaphragm structure according to claim 40, wherein said cover member is composed of a cover member substrate which consists of a tetragonal crystal, a mixture phase consisting of a cubic crystal and a tetragonal crystal, or a mixture phase consisting of a cubic crystal, a tetragonal crystal, and a monoclinic crystal.

42. A ZrO$_2$ flexible diaphragm structure according to claim 36, wherein said flexible member further comprises an intermediate ZrO$_2$ layer which has a cubic crystal content higher than that of said substrate and lower than that of said contact layer between said substrate and said contact layer.

43. The ZrO$_2$ flexible diaphragm structure according to claim 42, wherein said intermediate ZrO$_2$ layer contains said cubic crystal at a ratio not lower than 60% and not higher than 95%.

44. A ZrO$_2$ flexible diaphragm structure according to claim 42, further comprising a second intermediate ZrO$_2$ element which has a cubic crystal content higher than that of said substrate and lower than that of said contact layer between said supporting member and said contact layer.

45. The ZrO$_2$ flexible diaphragm structure according to claim 36, wherein a piezoelectric/electrostrictive element is disposed on a surface of said flexible member.

46. The ZrO$_2$ flexible diaphragm structure according to claim 36 which contains lead.

47. A fluid sensor which uses a ZrO$_2$ flexible diaphragm structure as claimed in claim 36.

48. A ZrO$_2$ flexible diaphragm structure according to claim 36, further comprising an intermediate ZrO$_2$ element which has a cubic crystal content higher than that of said substrate and lower than that of said contact layer between said supporting member and said contact layer.

49. A fluid sensor comprising:
a ZrO$_2$ flexible diaphragm structure according to claim 36;
a piezoelectric element having a piezoelectric film and at least a pair of electrodes disposed in contact with said piezoelectric film, on a first surface of said flexible member which is opposite a second surface of said flexible member which is in contact with said supporting member;
electrode terminals disposed on said second surface of said flexible member, said electrode terminals being electrically connected to said pair of electrodes;
a supporting element; and
a separating member maintaining said piezoelectric element and said supporting element in contactless conditions; wherein said separating member is disposed on said second surface of said flexible member so as to surround said piezoelectric element, and said flexible member is kept in contact and fixed with and to said supporting element by way of said separating member, wherein a glass layer is formed on said second surface of said flexible member.

50. The ZrO$_2$ flexible diaphragm structure according to claim 36, further comprising at least one piezoelectric element positioned on a surface of said flexible member opposite said contact layer.

51. The ZrO$_2$ flexible diaphragm structure according to claim 36, wherein said supporting member comprises ZrO$_2$ porcelain.

52. A waterproof ZrO$_2$ member to be used in an atmosphere containing water or water steam,
wherein a substrate is made of ZrO$_2$ which is composed of a tetragonal crystal, a mixture phase consisting of a cubic crystal and a tetragonal crystal, or a mixture phase consisting of a cubic crystal, a tetragonal crystal, and a monoclinic crystal, and
wherein a ZrO$_2$ layer which has a relative density (bulk density/theoretical density) not lower than 95% and contains at least 75% cubic crystal phase is disposed at a location to be exposed to an atmosphere containing water or water steam.

53. The waterproof ZrO$_2$ member according to claim 52, wherein the atmosphere containing water or water steam is an acidic atmosphere.

54. A ZrO$_2$ porcelain comprising:
a ZrO$_2$ porcelain flexible plate like member comprising a substrate and a contact part to be brought into contact with a liquid or a gas containing a liquid vapor;
a cylindrical member made of a ZrO$_2$ porcelain;
a connecting layer having a composition which is the same as that of said contact part, said connecting layer being formed on at least one end surface of said cylindrical member, said connecting layer being in contact with said plate like member, and
an intermediate ZrO$_2$ layer being positioned between said cylindrical member and said connecting layer or between said substrate and said contact part, said intermediate ZrO$_2$ layer having a cubic crystal content higher than that of said substrate or said cylindrical member and lower than that of said contact part or said connecting layer,
said contact part having a relative density (bulk density/theoretical density) not lower than 95% and containing at least 75% cubic crystal phase, said $ZrO_2$ porcelain flexible member being integrated with said cylindrical member which is a supporting member for the flexible member so that said contact part closes an opening of said cylindrical member.

55. A $ZrO_2$ porcelain as recited in claim 54, further comprising a second intermediate $ZrO_2$ layer having a cubic crystal content higher than that of said substrate or said cylindrical member and lower than that of said contact part or said connecting layer, said intermediate $ZrO_2$ layer being positioned between said cylindrical member and said connecting layer, said second intermediate $ZrO_2$ layer being positioned between said substrate and said contact part.

56. A $ZrO_2$ porcelain as recited in claim 54, wherein said intermediate $ZrO_2$ layer contains said cubic crystal phase at a ratio not lower than 60% and not higher than 95%.

57. A $ZrO_2$ porcelain as recited in claim 55, wherein said intermediate $ZrO_2$ layer and said second said intermediate $ZrO_2$ layer each contain said cubic crystal phase at a ratio not lower than 60% and not higher than 95%.

58. A fluid sensor comprising:
- a $ZrO_2$ porcelain flexible plate like member comprising a contact part to be brought into contact with a liquid or a gas containing a liquid vapor, said contact part having a relative density (bulk density/theoretical density) not lower than 95% and containing at least 75% cubic crystal phase;
- a cylindrical member made of a $ZrO_2$ porcelain, an end surface of said cylindrical member being in contact with said plate like member, said $ZrO_2$ porcelain flexible member being integrated with said cylindrical member which is a supporting member for the flexible member so that said contact part closes an opening of said cylindrical member;
- a piezoelectric element having a piezoelectric film and at least a pair of electrodes disposed in contact with said piezoelectric film, on the opposite surface of the surface where said cylindrical member is located;
- electrode terminals disposed on the opposite surface of the surface where said cylindrical member is located, of said $ZrO_2$ porcelain flexible member and electrically connected to said pair of electrodes;
- a supporting member; and
- a separating member maintaining said piezoelectric element and said supporting member in contactless conditions; wherein said separating member is disposed on the opposite surface of the surface where said cylindrical member is located, of said $ZrO_2$ porcelain flexible member so as to surround said piezoelectric element, and said $ZrO_2$ porcelain flexible member is kept in contact and fixed with and to said supporting member by way of said separating member,
- wherein a glass layer is formed on the opposite surface of the surface where said cylindrical member is located, of said $ZrO_2$ porcelain flexible member which is kept in contact with said separating member.

59. A $ZrO_2$ porcelain comprising:
- a $ZrO_2$ porcelain flexible plate like member comprising a substrate;
- a cylindrical member made of a $ZrO_2$ porcelain, an end surface of said cylindrical member being in contact with said flexible plate like member;
- a contact part having a relative density (bulk density/theoretical density) not lower than 95% and containing at least 75% cubic crystal phase being positioned on inside walls of an opening in said cylindrical member and on a surface of said substrate surrounded by a region of said contact between said flexible plate like member and said supporting member; and
- an intermediate $ZrO_2$ layer between said flexible plate like member and said contact part, or between said cylindrical member and said contact layer, said intermediate $ZrO_2$ layer having a cubic crystal content higher than that of said substrate or said cylindrical member and lower than that of said contact part,
- said $ZrO_2$ porcelain flexible member being integrated with said cylindrical member which is a supporting member for the flexible member.

60. The $ZrO_2$ porcelain according to claim 59, wherein said intermediate $ZrO_2$ layer contains said cubic crystal phase at a ratio not lower than 60% and not higher than 95%.

61. A fluid sensor comprising:
- a $ZrO_2$ porcelain flexible plate like member comprising a substrate;
- a cylindrical member made of a $ZrO_2$ porcelain, an end surface of said cylindrical member being in contact with said plate like member,
- a contact part having a relative density (bulk density/theoretical density) not lower than 95% and containing at least 75% cubic crystal phase being positioned on inside walls of an opening in said cylindrical member and on a surface of said substrate surrounded by a region of contact between said substrate and said supporting member,
- said $ZrO_2$ porcelain flexible member being integrated with said cylindrical member which is a supporting member for the flexible member;
- a piezoelectric element having a piezoelectric film and at least a pair of electrodes disposed in contact with said piezoelectric film, on the opposite surface of the surface where said cylindrical member is located, of said $ZrO_2$ porcelain flexible member;
- electrode terminals disposed on the opposite surface of the surface where said cylindrical member is located, of said $ZrO_2$ porcelain flexible member and electrically connected to said pair of electrodes;
- a supporting member; and
- a separating member maintaining said piezoelectric element and said supporting member in contactless conditions; wherein said separating member is disposed on the opposite surface of the surface where said cylindrical member is located, of said $ZrO_2$ porcelain flexible member so as to surround said piezoelectric element, and said $ZrO_2$ porcelain flexible member is kept in contact and fixed with and to said supporting member by way of said separating member,
- wherein a glass layer is formed on the opposite surface of the surface where said cylindrical member is located, of said $ZrO_2$ porcelain flexible member which is kept in contact with said separating member.

* * * * *